United States Patent [19] [11] 4,256,483
Asao et al. [45] Mar. 17, 1981

[54] 2-ALKOXY PYRIDAZINOQUINAZOLINONE DERIVATIVES AS HERBICIDES

[75] Inventors: Shuichiro Asao, Ashiya; Yoshinori Nakayama, Takarazuka; Ryo Yoshida, Kawanishi; Seizo Sumida, Nishinomiya; Shunichi Hashimoto, Toyonaka, all of Japan

[73] Assignee: Sumitomo Chemical Company, Limited, Osaka, Japan

[21] Appl. No.: 84,435

[22] Filed: Oct. 12, 1979

[30] Foreign Application Priority Data

Oct. 17, 1978 [JP] Japan ................... 53-128097

[51] Int. Cl.³ ............................................. A01N 43/58
[52] U.S. Cl. ........................................ 71/92; 544/234
[58] Field of Search ............................ 71/92; 544/234

[56] References Cited
PUBLICATIONS

Yanai et al., Chem. Abs. 63, 5638b (1965).
Beger et al., Chem. Abs. 60, 9276g (1964).

Primary Examiner—Mark L. Berch
Attorney, Agent, or Firm—Birch, Stewart, Kolasch & Birch

[57] ABSTRACT

A compound of the formula:

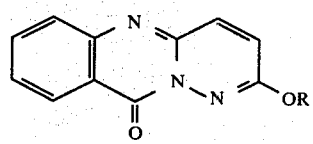

wherein R is a methyl group or an ethyl group shows a strong herbicidal activity against a wide variety of weeds without any material chemical injury to crop plants.

2 Claims, No Drawings

2-ALKOXY PYRIDAZINOQUINAZOLINONE DERIVATIVES AS HERBICIDES

The present invention relates to use of substituted pyridazinoquinazolinone derivatives as herbicides.

The said substituted pyridazinoquinazolinone derivatives, i.e. 2-alkoxy-10H-pyridazino[3,2-b]quinazolin-10-ones, are representable by the formula:

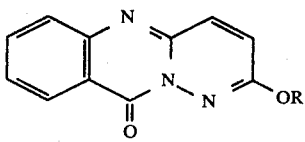

wherein R is a methyl group or an ethyl group. They are already known [K. Yanai et al.: Yakugaku Zasshi (Bull. Pharm. Soc. Japan), 85, 339 (1965)], but their biological activity has never been reported.

In the course of an extensive study for development of excellent herbicides, it has now been unexpectedly found that the substituted pyridazinoquinazolinone derivatives (I) exhibit a strong herbicidal activity against a wide variety of weeds without any notable chemical injury onto crop plants such as cotton, soybean, corn, wheat and rice.

The substituted pyridazinoquinazolinone derivative (I) can be produced by reacting 2-chloro-10H-pyridazino-[3,2-b]quinazolin-10-one (II) with an alkanol (III) in the presence of a strong base as shown in the following formulae:

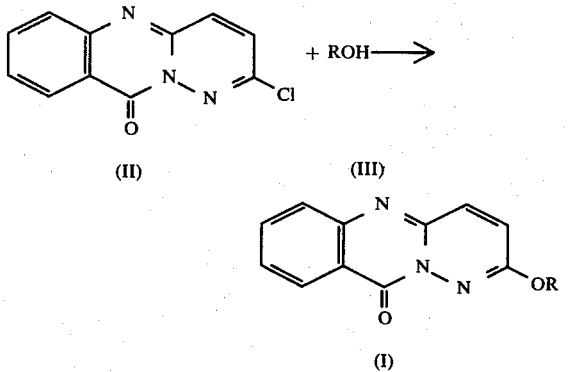

wherein R is as defined above.

For instance, a mixture of 2-chloro-10H-pyridazino[3,2-b]quinazolin-10-one (II) and sodium hydroxide in methanol is stirred at room temperature or while heating. The reaction mixture is distilled to remove the methanol and then made acidic to give the reaction product as crystals.

Alternatively, the substituted pyridazinoquinazolinone derivative (I) may be produced by reacting 2-chloro-10H-pyridazino[3,2-b]quinazolin-10-one (II) with an alkoxide in an alkanol as shown in the following formulae:

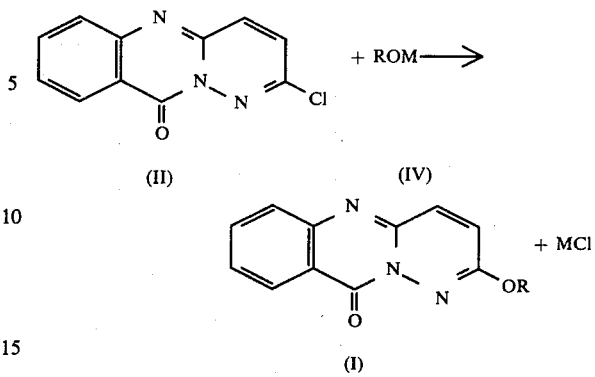

wherein R is as defined above and M is an alkali metal.

For instance, a mixture of 2-chloro-10H-pyridazino[3,2-b]quinazolin-10-one (II) and sodium methoxide in methanol is stirred at room temperature or while heating. The reaction mixture is distilled to remove the methanol and made acidic with an aqueous solution of acetic acid to give the reaction product.

Practical embodiments of the production of the substituted pyridazinoquinazolinone derivatives (I) are illustratively shown in the following Reference Examples.

REFERENCE EXAMPLE 1

To 1.2 g of 2-chloro-10H-pyridazino[3,2-b]quinazolin-10-one dissolved in ethanol, there was added a solution of sodium hydroxide (2.0 g) in water (8 ml), and stirring was continued at 40° C. for 2 hours. After completion of the reaction, the solvent was removed by distillation, followed by addition of an aqueous solution of acetic acid. The precipitates were collected by filtration and recrystallized from a mixture of methanol and water to give 1.0 g of 2-ethoxy-10H-pyridazino[3,2-b]quinazolin-10-one (Compound No. 2). M.P., 159.5°–160.5° C.

Elementary analysis: Cacld. for $C_{13}H_{11}O_2N_3$: C, 64.73%; H, 4.56%; N, 17.43%. Found: C, 64.65%; H, 4.48%, N, 17.52%.

REFERENCE EXAMPLE 2

2-Chloro-10H-pyridazino[3,2-b]quinazolin-10-one (2.3 g) and sodium methoxide (1.1 g) in 100 ml of methanol was heated at 60° C. for 5 hours. After completion of the reaction, the solvent was removed by distillation, followed by addition of an aqueous solution of acetic acid. The precipitates were collected by filtration and recrystallized from methanol to give 1.6 g of 2-methoxy-10H-pyridazino[3,2-b]-quinazolin-10-one (Compound No. 1). M.P., 222.5°–223.0° C.

Elementary analysis: Calcd. for $C_{12}H_9O_2N_3$: C, 63.43%; H, 3.99%; N, 18.49%. Found: C, 63.50%; H, 3.84%; N, 18.40%.

The substituted pyridazinoquinazolinone derivatives (I) of the invention show a strong herbicidal activity against a wide variety of weeds. For instance, they can exert a notable controlling or exterminating activity by soil treatment before germination or foliage treatment after germination on dicotyledonous and monocotyledonous plants, of which typical examples are as follows: common lambsquarters (*Chenopodium alubum*), redroot pigweed (*Amaranthus retroflexus*), ladysthumb (*Polygonum sp.*), chickweed (*Stellaria media*), common groundsel (*Senecio vulgaris*), common purslane (*Portulaca oleracea*), cocklebur (*Xanthium pennsylvanicum*), Jimsonweed (*Datura stramonium*), velvet-leaf (*Abutilon theopharasti*), morningglory (*Ipomea purpurea*), sesbania (*Sesbania exaltata*), prickly sida (*Sida spinosa*), sicklepod (*Cassia obtusifolia*), hairy galinsoga (*Galinsoga ciliata*), barnyard grass (*Echinochloa crusgalli*), green foxtail (*Setaria viridis*), large crabgrass (*Digitaria sanguinalis*), fall panicum (*Panicum dichotomiflorum*), annual bluegrass (*Poa annua*), goosegrass (*Eleucine indica*), downy brome (*Bromus tectorum*), wild oat (*Avena fatua*), Johnsongrass (*Sorghum halepense*), quackgrass (*Agropyron repens*), etc.

Advantageously, the substituted pyridazinoquinazolinone derivatives (I) do not produce any material chemical injury on various crop plants such as cotton, soybean, corn, wheat or rice, so that they are useful as selective herbicides applicable to fields of those crop plants. It is particularly notable that they exhibit a high selectivity to cotton not only by soil treatment before germination but also by foliage treatment after germination. Further, they can be applied to paddy rice plants under a flooded condition. An appropriate selection of their dosage will realize a total prevention or control of the weeds in non-agricultural lands because of their strong herbicidal activity.

The dosage of the substituted pyridazinoquinazolinone derivatives (I) may vary depending on their actual use but, in general, they can be applied within a range from about 1 to 200 g per are, preferably from about 5 to 100 g per are. In the preparation of a herbicidal composition, the content of the substituted pyridazinoquinazolinone derivative (I) may be usually from 1 to 90% by weight, preferably from 2 to 80% by weight.

In the practical usage of the substituted pyridazinoquinazolinone derivatives (I), they may be applied as such or in any preparation form such as dusts, granules, fine granules, wettable powders or emulsifiable concentrates.

On formulation of such preparations, a solid or liquid carrier may be used. As for the solid carrier, there may be mentioned mineral powders (e.g. kaolin, bentonite, clay, montmorillonite, talc, diatomaceous earth, mica, vermiculite, gypsum, calcium carbonate, apatite), vegetable powders (e.g. soybean powder, flour, wooden powder, tobacco powder, starch, crystalline cellulose), high molecular weight compounds (e.g. petroleum resin, polyvinyl chloride, dammar gum, ketone resin), alumina, wax and the like. As for the liquid carrier, there may be exemplified alcohols (e.g. methanol, ethanol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methylethylketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

A surface active agent used for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethylene-oxypropylene polymers, polyoxyethylene alkyl phosphates, fatty acid salts, alkyl sulfates, alkyl sulfonates, alkylaryl sulfonates, alkyl phosphates, polyoxyethylene alkyl sulfates and the like. But, the surface active agent is not of course limited to these compounds. And, if necessary, gelatin, casein, sodium alginate, starch, agar, polyvinyl alcohol or the like may be used as an auxiliary agent.

In addition to agricultural chemicals ordinarily employed such as wetting agents, the substituted pyridazinoquinalolinone derivatives (I) may also be used together with other herbicides, microbicides, pyrethroid series insecticides, other insecticides, fungicides, plant growth regulators, fertilizers, etc. to improve their herbicidal activity. As the other herbicides, there may be exemplified DCMU (diuron), linuron, fluometuron, prometryne, MSMA (monosodium methanearsenate), DSMA, dalapon, methazol, etc.

Practical embodiments of the herbicidal composition according to the invention are illustratively shown in the following Examples wherein parts and % are by weight.

PREPARATION EXAMPLE 1

Fifty parts of Compound No. 1, 5 parts of alkylbenzenesulfonate as a wetting agent and 45 parts of diatomaceous earth are well mixed while being powdered to obtain a wettable powder.

PREPARATION EXAMPLE 2

Ten parts of Compound No. 1, 30 parts of cyclohexanone, 40 parts of dimethylformamide and 20 parts of polyoxyethylene alkylaryl ether are well mixed to obtain an emulsifiable concentrate.

PREPARATION EXAMPLE 3

Ten parts of Compound No. 2 and 90 parts of clay are well mixed to obtain a dust.

PREPARATION EXAMPLE 4

Five parts of Compound No. 2, 7 parts of ligninsulfonate and 88 parts of clay are well mixed while being powdered. The mixture is then kneaded with water, granulated and dried to obtain a granule.

PREPARATION EXAMPLE 5

Eighty parts of Compound No. 1, 5 parts of alkylbenzenesulfonate as a wetting agent and 15 parts of diazomaceous earth are well mixed while being powdered to obtain a wettable powder.

PREPARATION EXAMPLE 6

Two parts of Compound No. 2 and 98 parts of clay are well mixed to obtain a dust.

PREPARATION EXAMPLE 7

Two parts of Compound No. 2, 10 parts of ligninsulfonate and 88 parts of clay are well mixed while being powdered. The mixture is then kneaded with water, granulated and dried to obtain a granule.

The application of the substituted pyridazinoquinazolinone derivatives (I) as herbicides will be illustrated in the following Examples wherein the phytotoxicity to crop plants and the herbicidal activity against weeds were evaluated as follows:

The aerial parts of treated test plants were cut off and weighed (fresh weight); the percentage of the fresh weight of the treated plot to that of the untreated plot was calculated. The phytotoxicity to cultivated plants and the herbicidal activity against weeds were expressed in numerals 0 to 5 according to the criteria shown in the following table. The rating values 0 and 1 in phytotoxicity and 5 and 4 in herbicidal activity are respectively regarded as showing a satisfactory safety to cultivated plants and as showing a satisfactory effect in controlling weeds. Exceptionally, the rating values in the test for paddy rice plants were calculated from the dry weight of plants.

| Rating value | Fresh weight (percentage to untreated plot) | |
|---|---|---|
| | Crop plant | Weeds |
| 5 | 0–39 | 0 |
| 4 | 40–59 | 1–10 |
| 3 | 60–79 | 11–20 |
| 2 | 80–89 | 21–40 |
| 1 | 90–99 | 41–60 |
| 0 | 100 | 61–100 |

The following control compounds were used in the examples.

Fluometuron:

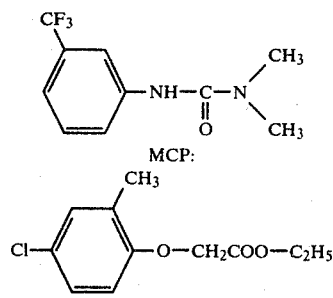

MCP:

EXAMPLE I

Herbicidal activity by post-emergence treatment)

Plastic trays (35×25×10 cm (in depth)) were filled with upland soil, and the seeds of cotton, corn and rice as well as the seeds of weeds such as redroot pigweed, common lambsquarters, velvetleaf, sunflower, cocklebur, morningglory, black nightshade (*Solanum nigrum*), large crabgrass, barnyardgrass (*Echinochloa crus-galli*) and green foxtail were sowed in each of the trays and cultivated for 3 weeks in a greenhouse kept at 25° C. The designed amount of the test compound was sprayed to the foliage over the top of the test plants by means of a small hand sprayer. Two weeks thereafter, the phytotoxicity and the herbicidal activity of the test compound were examined. The results are shown in Table 1.

On the above-mentioned foliar application, the test compound formulated into an emulsifiable concentrate was dispersed in water to make a spray volume of 5 liters per are, and a non-ionic wetting agent was added thereto to make a final concentration of 1%. At this foliar application, cotton was in the primary leaf stage, corn in the three-leaf stage and rice in the second-leaf stage. The weeds were, with variation depending upon the species, at the 2- to 4-leaf stage and had a height of 2 to 12 cm.

TABLE 1

| | Phytotoxicity and herbicidal activity (active ingredient, 20 g/are) | | |
|---|---|---|---|
| Test plant | Compound No. 1 | Compound No. 2 | Fluometuron |
| Cotton | 0 | 0 | 1 |
| Corn | 1 | 1 | 3 |
| Rice | 0 | 0 | 3 |
| Redroot pigweed | 5 | 5 | 5 |
| Common lambsquarters | 5 | 5 | 5 |
| Velvetleaf | 5 | 5 | 5 |
| Sunflower | 5 | 5 | 5 |
| Cocklebur | 5 | 5 | 5 |
| Morningglory | 5 | 5 | 5 |
| Black nightshade | 5 | 5 | 5 |
| Large crabgrass | 5 | 4 | 4 |
| Barnyardgrass | 4 | 4 | 3 |
| Green foxtail | 4 | 4 | 3 |

EXAMPLE II (Herbicidal activity by pre-emergence treatment)

Plastic trays (35×25×10 cm (in depth)) were filled with upland soil, and the seeds of soybean, cotton, corn, wheat and rice as well as the seeds of weeds such as redroot pigweed, common lambsquarters, wild mustard (*Brassica arvensis*), Jimsonweed, velvetleaf, black nightshade and green foxtail were separately sowed in the trays. The test compound formulated into an emulsifiable concentrate was dispersed in water to make a spray volume of 5 liters per are and sprayed to the whole surface of the soil by means of a small hand sprayer. After the spraying, the test plants were cultivated for 3 weeks in a greenhouse kept at 25° C., and the phytotoxicity and the herbicidal activity were examined. The examination was carried out by the same criteria as described above.

The results are shown in Table 2.

TABLE 2

| | Phytotoxicity and herbicidal activity | | |
|---|---|---|---|
| Test plant | Compound No. 1 (active ingredient, 20 g/are) | Compound No. 2 (active ingredient, 40 g/are) | Fluometuron (active ingredient, 20 g/are) |
| Soybean | 0 | 0 | — |
| Cotton | 0 | 0 | 0 |
| Corn | 0 | 0 | — |
| Wheat | 0 | 0 | — |
| Rice | 0 | 0 | — |
| Redroot pigweed | 5 | 5 | 5 |
| Common lambsquarters | 5 | 5 | 5 |
| Wild mustard | 5 | 4 | 5 |
| Jimsonweed | 5 | 5 | 5 |
| Velvetleaf | 5 | 4 | 5 |
| Black nightshade | 5 | 5 | 5 |
| Green foxtail | 4 | 4 | 4 |

EXAMPLE III (Paddy rice test)

Wagner's pots (1/5000 are) were each filled with paddy field soil containing the seeds of weeds and kept under flooded conditions. Seedlings of rice plants at the three-leaf stage were transplanted thereto and cultivated for 5 days. Thereafter, a required amount of the granule of each test compound was applied to the soil under flooded conditions. Twenty-five days thereafter, the evaluation of the phytotoxicity to rice plants and the herbicidal activity against barnyardgrass, broad-leaved weeds such as false pimpernel, tooth cup and pickerel weed, and nutsedge sp. (*Cyperus serotinus*) were made.

The results are shown in Table 3.

TABLE 3

| Test plant | Phytotoxicity and herbicidal activity (active ingredient, 20 g/are) | | |
|---|---|---|---|
| | Compound No. 1 | Compound No. 2 | MCP |
| Rice | 0 | 0 | 3 |
| Barnyardgrass | 5 | 4 | 4 |
| Broad-leaved weeds | 5 | 5 | 5 |
| Nutsedge sp. | 5 | 5 | 5 |

What is claimed is:

1. A herbicidal composition which comprises as an active ingredient a herbicidally effective amount of at least one of the compounds of the formula:

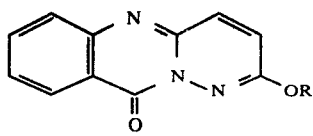

wherein R is a methyl group or an ethyl group, and an agriculturally acceptable inert carrier or diluent.

2. A method for controlling or exterminating weeds which comprises applying the herbicidal composition according to claim 1 to the area where the weeds grow.

* * * * *